(12) United States Patent
Malmquist et al.

(10) Patent No.: US 10,598,640 B2
(45) Date of Patent: Mar. 24, 2020

(54) METHOD FOR BASELINE CORRECTION IN A CHROMATOGRAM

(71) Applicant: GE Healthcare Bio-Sciences AB, Uppsala (SE)

(72) Inventors: Gunnar Malmquist, Uppsala (SE); Martin Hall, Uppsala (SE); Nils Stafstrom, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 127 days.

(21) Appl. No.: 15/066,429

(22) Filed: Mar. 10, 2016

(65) Prior Publication Data
US 2016/0282318 A1 Sep. 29, 2016

(30) Foreign Application Priority Data
Mar. 27, 2015 (GB) .................................. 1505229.3

(51) Int. Cl.
*G01N 30/86* (2006.01)
*G01N 30/74* (2006.01)
*G01N 30/34* (2006.01)

(52) U.S. Cl.
CPC ......... *G01N 30/8624* (2013.01); *G01N 30/34* (2013.01); *G01N 30/74* (2013.01)

(58) Field of Classification Search
None
See application file for complete search history.

(56) References Cited

U.S. PATENT DOCUMENTS 4,357,668 A * 11/1982 Schwartz ............... H03K 5/084
                                                               210/198.2
4,802,102 A * 1/1989 Lacey ................ G01N 30/8624
                                                               702/32

(Continued)

OTHER PUBLICATIONS

Quintas et al., "Univariate Method for Background Correction in Liquid Chromatography—Fourier Transform Infrared Spectrometry", Journal of Chromatography A; vol. 1190, 2008. pp. 102-109.

(Continued)

*Primary Examiner* — Nimeshkumar D Patel
*Assistant Examiner* — Jean F Morello
(74) *Attorney, Agent, or Firm* — Eversheds Sutherland (US) LLP

(57) ABSTRACT

The invention discloses a method for correcting a baseline in a chromatogram obtained using a buffer with at least one UV-absorbing component which is a weak acid or a weak base. The method comprises the steps of:
a) providing a chromatography system with a chromatography column and a UV detector downstream of the chromatography column;
b) providing UV extinction coefficients at a wavelength λ for the acid form and the base form of the UV-absorbing component(s) and a dissociation constant for the component(s),
c) obtaining a chromatogram with the UV detector at wavelength λ using the buffer under a set of conditions where pH and/or conductivity is varied between these conditions,
d) for a plurality of said conditions calculating the concentrations of the acid and base forms using the dissociation constant(s) and values for pH and conductivity values, and
e) calculating UV absorption values of the acid and base forms from the concentrations and UV extinction coefficients under the conditions in question and subtracting the UV absorption values from the chromatogram.

14 Claims, 5 Drawing Sheets

(56) References Cited

U.S. PATENT DOCUMENTS

| | | | | |
|---|---|---|---|---|
| 5,076,909 A * | 12/1991 | Overfield | ............. | C10G 11/187 |
| | | | | 208/177 |
| 6,221,250 B1 * | 4/2001 | Stafstrom | ............... | G01N 30/34 |
| | | | | 210/101 |
| 7,257,987 B2 * | 8/2007 | O'Brien | ............... | G01N 1/2202 |
| | | | | 73/23.22 |
| 8,771,597 B2 * | 7/2014 | Zochbauer | ............. | G01N 21/05 |
| | | | | 356/51 |
| 2007/0135343 A1 * | 6/2007 | Webb | .................... | A61K 9/0019 |
| | | | | 424/680 |
| 2010/0050737 A1 * | 3/2010 | Wolters | .............. | G01N 30/8665 |
| | | | | 73/23.22 |
| 2011/0039712 A1 | 2/2011 | Bjorkesten et al. | | |
| 2013/0210164 A1 * | 8/2013 | Gagnon | ................... | G01N 1/34 |
| | | | | 436/177 |
| 2013/0238254 A1 | 9/2013 | Nakamura | | |
| 2013/0270492 A1 * | 10/2013 | Carredano | ............. | G01N 27/06 |
| | | | | 252/519.3 |
| 2014/0179008 A1 * | 6/2014 | Lin | ........................ | G01N 30/34 |
| | | | | 436/18 |

OTHER PUBLICATIONS

EP Search Report from corresponding GB application No. 1505229.3 dated Dec. 18, 2015; 5 pages.

\* cited by examiner

METHOD FOR BASELINE CORRECTION IN A CHROMATOGRAM

TECHNICAL FIELD OF THE INVENTION

The present invention relates to the field of liquid chromatography, and more particularly to a method for correction of baselines in a chromatogram. It also relates to a computer program and a chromatography system for carrying out the method.

BACKGROUND OF THE INVENTION

The most common method for detection of eluted species in liquid chromatography is to measure the ultraviolet absorbance in a flow-through cell located downstream of the column outlet. If any component in the mobile phase has a significant absorbance at the detection wavelength, this will give rise to a non-zero baseline in the chromatogram, which can however be simply offset if the baseline is constant. If the column is eluted with a mobile phase gradient where one component in the gradient shows UV absorbance, an increasing or decreasing baseline will be formed, for which correction methods have been suggested in e.g. EP299652A1.

A more complex situation often occurs in the chromatography of proteins and other biomacromolecules, where aqueous buffers are normally used as mobile phases and it is common to vary the pH and/or the ionic strength during elution. Many buffer components, in particular carboxylic acids, have different UV spectra for the acid and the base form and thus the UV absorbance varies with pH and also with the ionic strength, which affects the dissociation equilibria. This gives rise to baseline variations which are not simply monotonic and there is thus a need for correction of these variations to simplify the evaluation of the chromatograms.

SUMMARY OF THE INVENTION

One aspect of the invention is to provide a method for correction of chromatograms obtained using buffers with at least one UV-absorbing component which is a weak acid or a weak base. This is achieved with a method as defined in claim 1.

One advantage is that the correction can be made without having to perform any blank runs. A further advantage is that the method can be used for a wide range of different elution profiles.

Further suitable embodiments of the invention are described in the dependent claims.

DETAILED DESCRIPTION OF EMBODIMENTS

Figure 1:
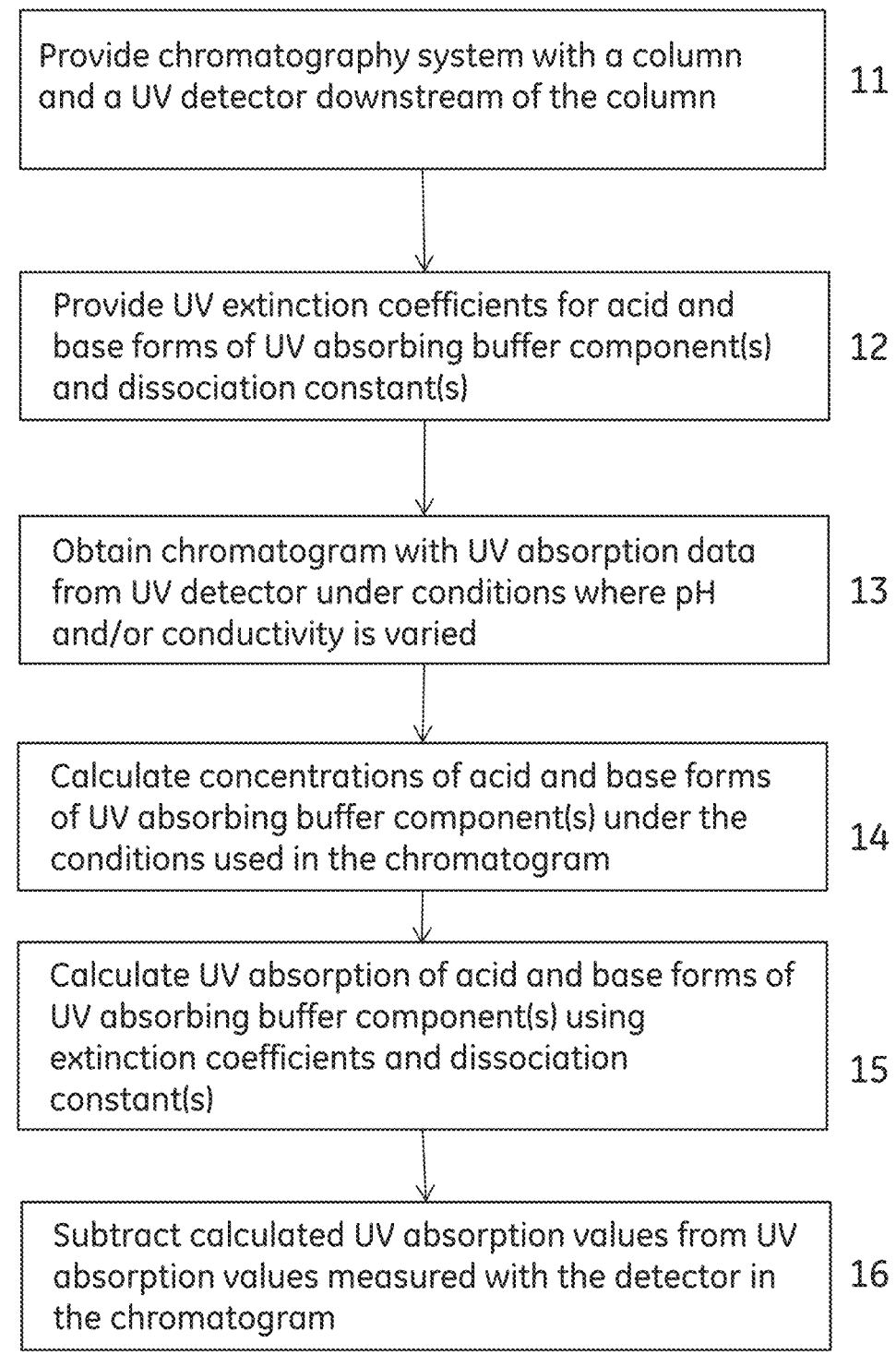
FIG. 1 shows the method of the invention.
Figure 2:
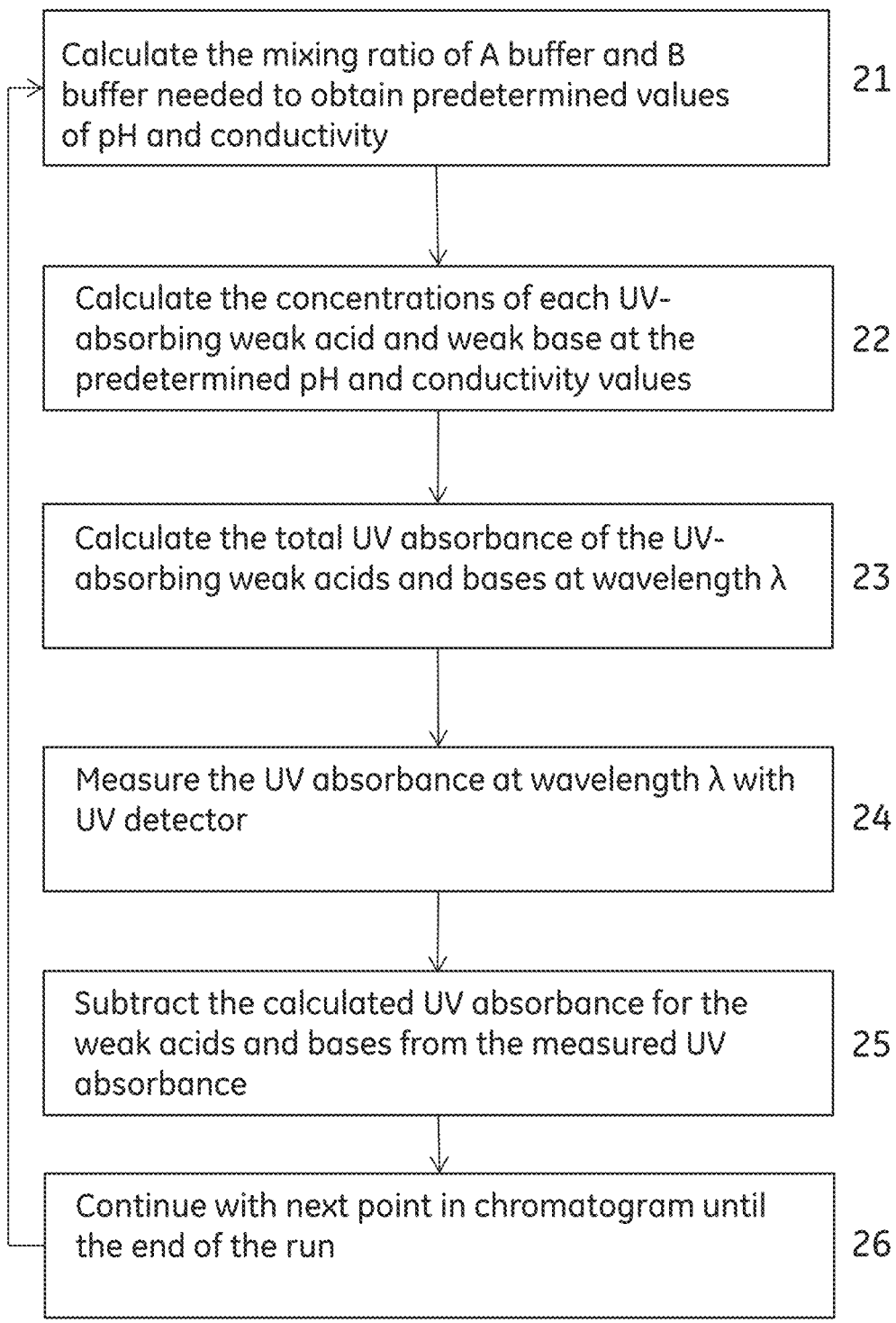
FIG. 2 shows an example of a method of the invention for calculation of UV baseline corrections based on predetermined pH and conductivity values.
Figure 3:
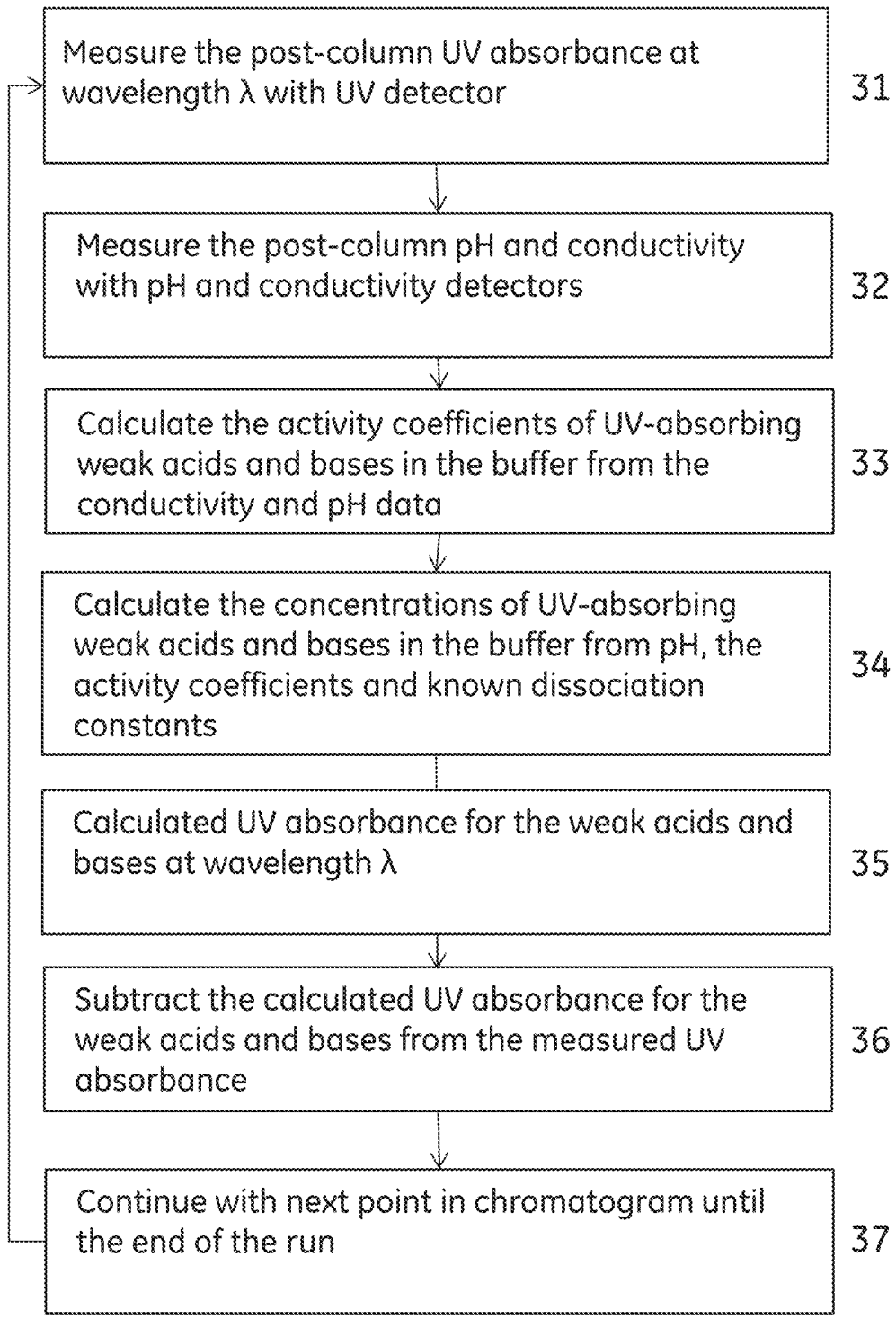
FIG. 3 shows an example of the method of the invention for calculation of UV baseline corrections based on measured pH and conductivity values.

In one aspect, illustrated by FIGS. 1-3, the present invention discloses a method for correcting a baseline in a chromatogram obtained using a buffer (mobile phase) with at least one UV-absorbing component which is a weak acid or a weak base. The method comprises the steps of:
a) providing a chromatography system with a chromatography column and a UV detector downstream of the chromatography column. The UV detector can suitably have a flow cell in fluidic connection with an outlet of the chromatography column. The chromatography column can be a packed bed chromatography column, but it can also be e.g. a membrane adsorber, a monolithic column or an expanded bed column.
b) providing UV extinction coefficients at a wavelength λ for the acid form and the base form of the UV-absorbing component(s) and a dissociation constant for the component(s).
c) obtaining a chromatogram with a UV detector at wavelength λ using the buffer under a set of conditions where pH and/or conductivity is varied between these conditions. The conditions may cover a range of pH and/or conductivity values, such as the range between start values and end values for pH and conductivity. Each specific condition may be a point within such a range, with a specific pH and/or conductivity value. In the chromatogram, UV absorption values measured by the UV detector are typically plotted versus time or volume of buffer/mobile phase.
d) for a plurality of the conditions calculating the concentrations of the acid and base forms using the dissociation constant(s) and values for pH and/or conductivity values, and
e) calculating UV absorption values of the acid and base forms from the concentrations and UV extinction coefficients under the conditions in question and subtracting the calculated UV absorption values from the chromatogram. The calculated UV absorption values are suitably subtracted from the UV absorption values measured by the UV detector under the same conditions.

Methods for the calculation of concentrations of corresponding acid forms and base forms at moderate ionic strengths (up to 100 mM) are documented in the literature and are based on the algebraic or computer based solution of the equations of equilibrium among the various charged and uncharged species present in the buffer solution.

For a particular basic species (which can be a base B or a conjugate base $A^-$) in equilibrium with a corresponding acidic species (which can be a conjugate acid $BH^+$ or an acid HA, respectively) the equilibrium can be written $$H^+ + \text{basic species} \Leftrightarrow \text{acidic species}^+ \quad \text{Eq 1.1}$$

The corresponding dissociation constant (equilibrium constant) $K_a$ is defined as $$K_a = (H^+)(\text{basic species})/(\text{acidic species}^+) \quad \text{Eq 1.2}$$

wherein the parenthesis denotes the activities of each species. Taking the logarithms of both side of Eq. 1.2 and solving for the pH defined as $-\log(H^+)$ gives $$pH = pKa + \log\{(\text{basic species})/(\text{acidic species})\} \quad \text{Eq 1.3}$$

which is sometimes known as the Henderson-Hasselbach equation. The reason why the activities are to be used in Eq 1.2 rather than the corresponding concentrations is that due to mainly electrostatic interactions, the ions involved tend to become shielded from the environment. However, whereas pH measurements are direct observations of the activity of the protons, it is rather the concentrations and not the corresponding activities of the buffer ions which are observed for instance by weighing, pipetting or pumping their amounts and volumes. According to Beer's law, the UV absorbance of a solution is also proportional to the concentration of a UV-absorbing species. The activity of each ion is related to the corresponding concentration through the activity coefficient $\varphi$ $$(species) = \varphi[species] \qquad Eq\ 1.4$$

At the ideal state of infinite dilution, $\varphi$ becomes 1 and the activity of every ion become equal to the corresponding concentration. However, in real cases, the ionic strength is different from 0 and the activity coefficients of the different species become less than 1.

In certain embodiments, the concentrations of said acid and base forms are calculated using the equation of Debye-Hückel, known as $$-\log \varphi = (AZ^2 I^{0.5})/(1+0.33*10^8 a I^{0.5}) \qquad Eq\ 1.5$$

wherein A is a constant, or rather a temperature dependent parameter ~0.51. Using well known data, the value of A can accurately be calculated as $A=0.4918+0.0007*T+0.000004*T^2$ where T is the temperature in degrees Celsius. Z is the charge of the ion and the quantity a, the radii of the hydrated ions (in A), is described as the "mean distance of approach of the ions, positive or negative" in the original paper of Debye and Hüickel (P Debye, E Hüickel: Physikalische Zeitschrift 24: 185-206, 1923), although it is also known as the ion size parameter. The ion size parameter has been shown to be different for different ionic species. I is the ionic strength $$I = \frac{1}{2}\Sigma(C_i Z_i^2) \text{(includes all ions)} \qquad Eq\ 1.6$$

$C_i$ is the concentration and $Z_i$ is the charge of ion present in the solution (in units of electronic charge).

Inserting Eq 1.4 into Eq 1.3 gives the pH in terms of the concentrations instead of the activities:

$$\begin{aligned} pH &= pK_a + \log\{\varphi_b[\text{basic species}]/(\varphi_a[\text{acidic species}])\} \\ &= pK_a + \log\varphi_b - \log\varphi_a + \log\{[\text{basic species}]/[\text{acidic species}]\} \\ &= pK'_a + \log\{[\text{basic species}]/[\text{acidic species}]\} \end{aligned} \qquad Eq\ 1.7$$

Where $$pK'_a = pK_a + \log\varphi_b - \log\varphi_a \qquad Eq\ 1.8$$

is an apparent $pK_a$ value which allows the use of the measurable values of the concentrations of the different buffer species. The value of $pK_a'$ can be calculated inserting Eq 1.5 into Eq 1.8 giving $$pK_a' = pK_a + (AZ_a^2 I^{0.5})/(1+0.33*10^8 a_a I^{0.5}) - (AZ_b^2 I^{0.5})/(1+0.33*10^8 a_b I^{0.5}) \qquad Eq\ 1.9$$

where the introduction of the subscripts a and b was necessary to specify the parameters corresponding to the acid and the base respectively. Thus
$Z_a$=Charge of acidic species
$Z_b$=Charge of basic species
$a_a$=ion size parameter of the acidic species
$a_b$=ion size parameter of the acidic species Applied to pH calculations, the Debye-Hückel theory results in the modification of the $pK_a$ values of the buffers (known as the thermodynamic pKa values) into corresponding $pK_a'$ values given by Eq 1.9. Most of the parameters in Eq 1.9 are straight forward to estimate. The most challenging parameter is a.

Guggenheim & Schindler (see Guggenheim E A & Schindler T D. (1934) *J. Phys. Chem.* 33. 533), have suggested an approximation of the parameter a set to 3 Å for all buffer molecules leading to the somewhat simplified formula $$pK_a' = pK_a + (AZ_a^2 I^{0.5})/(1+I^{0.5}) - (AZ_b^2 I^{0.5})/(1+I^{0.5}) \qquad Eq\ 1.10$$

Eq 1.10 above is the formula for ionic strength correction usually found in the literature. Sometimes correction terms are added to the right hand side of this equation to compensate for accuracy loss at higher ionic strengths for various buffers. However, the accuracy obtained by doing this is poor when the ionic strength is as high as 1M, which is within commonly used ranges in gradient elution in for instance ion exchange chromatography and HIC.

Kielland (Jacob Kielland in Activity Coefficients of Ions in Aqueous Solutions, September 1937) has studied activity coefficients of ions in liquids and provides an extended table of ionic activity coefficients, taking into consideration the diameter of the hydrated ions. The data presented by Kielland for the hydrated ion size parameter $a_i$ was obtained using four different models: Bonino's model which takes into account the crystal radius and deformability; the well-known equation $108a_i=182z_i/I_\infty$ which takes ionic mobilities into consideration; the empirical modification thereof by Brull, and finally the Ulrich entropy deficiency method. Rounded average values of said four models were used to obtain the data reported in that study. The $a_i$ values presented by Kielland present a substantial variation, from 2.5 to as much as 11, and non-general models are suggested for the activity coefficient based on this variation dependent upon the nature of the ions i.e. one equation for inorganic ions and one different equation for organic ions.

U.S. Pat. No. 6,221,250 relates to a method of preparing liquid mixtures which advantageously utilizes the above-discussed approximation of the parameter a. More specifically, the disclosed method of preparing a mixture comprises the following components: (i) one or more buffering species; (ii) an acid or alternatively a base; (iii) optionally a salt; and (iv) a solvent. The proportions of the components (i) to (iv) are concomitantly varied in such a way as to take account of the interrelationship of the pH and the ionic strength of the liquid mixture to obtain at each moment a preselected pH of the mixture, and the method is based on the use of a modified and repetitive Guggenheim-Schindler equation wherein buffer specific correction factors are used for attainment of constant pH along a gradient. Thus, in certain situations, a disadvantage of this method can be that if a new buffer needs to be introduced; calculations need to be made again.

The ion size parameter a in the Debye-Hückel equation can in some embodiments be determined as a weighted mean ion size of all species contributing significantly to the ionic strength of the buffer, and the ionic strength of each of these species can be used as weighting parameter. Specifically, the ion size parameter a of the Debye-Hückel equation can be determined as $$a = \frac{\sum I_i a_i}{I} \qquad Eq.\ 1.11$$

wherein $I_i$ is the ionic strength and $a_i$ the ion size parameter of species i and I the total ionic strength. wherein Ii is the ionic strength and $a_i$ the ion size parameter of species i, and I the total ionic strength defined in Equation 1.6 above. Starting from said equation then:

$$I_i = \frac{1}{2} Z_i^2 C_i \qquad \text{Eq. 1.12}$$

The ion size parameter $a_i$ of species i is an experimentally established or approximated value, and examples of $a_i$ values for some buffers and salts are listed in US20110039712 table 2 p. 10.

Throughout this disclosure the term "species" covers any and all ions or molecules that contribute to the ionic strength of the liquid mixture, and more specifically one component, e.g. a buffer system such as a weak acid, may correspond to two or more species of different charge, each with an associated $a_i$ value. Due to the fact that $a_i$ is related to the "ion size" in a specific environment, it has been found that the $a_i$ value of one specific species may be different for different combinations of components, e.g. buffer, salt etc. For example, it has been found that the $a_i$ values for NaCl are different when mixed with a phosphate buffer compared to an acetate buffer, as is shown in US20110039712 table 2 p. 10. However, it has been found that the $a_i$ values are valid for tested component combinations over a wide range of pH and Ionic strengths using the present method, resulting in improved predictability over essentially the whole ranges.

Alternatively, the ion size parameter a of the Debye-Hückel equation can be approximated as $$a = 0.5*(\text{mass})^{1/3} + \text{shell}.$$

wherein "shell" optionally is fixed at one value for a positively charged species and fixed at a different value for a negatively charged species, and optionally fixed at a value in the range of 3.8-4.2, such as 4.0, for positively charged ionic species; and "shell" is fixed at a value in the range of 0-0.2, such as 0, for negatively charged ionic species. These calculation models are described in more detail in US20110039712, which is hereby incorporated by reference in its entirety.

In some embodiments, the concentrations of the acid and base forms are calculated using an iterative procedure. The iterative procedure can e.g. comprise:
i) determining the concentrations wherein a pre-defined ionic strength of the liquid mixture is addressed to the species according to a pre-defined distribution among the species;
ii) on the basis of the concentrations determined in the preceding step, calculating the ionic strength of each species in the buffer;
iii) determining a new set of concentrations; taking account of the ionic strength calculated in ii), and
iv) repeating the steps ii) and iii) until a predetermined convergence criterion is met.

The addressing of the pre-defined ionic strength of the liquid mixture among the species, in step (i), is pre-defined to achieve a suitable starting point for the iterative process in order to achieve quick convergence and to avoid false convergence. According to one embodiment the pre-defined ionic strength of the liquid mixture is addressed to the salt species, as they normally are dominant contributors to the total ionic strength of a buffer comprising a salt component. For liquid mixtures, without any salt component, the pre-defined ionic strength of the liquid mixture is addressed.

In step (ii), the relative component proportions determined in the preceding step, i.e. step (i) in the first iteration and step (iii) in the subsequent iterations, are used to calculate the ionic strength of each species in the mixture. Hence, the concentration of each species as defined by the relative component proportions is used to calculate a more correct ionic strength distribution, which subsequently is used to determine more correct relative component proportions (step (iii)) and so on until convergence.

The predetermined convergence criteria may be selected to be any suitable criteria that ensure that the relative component proportions are defined with sufficient accuracy, at a reasonable computational effort. According to one embodiment, the convergence criteria may be selected to be the iteration step when the deviation between the last set of relative component proportions and the set found in the immediately preceding step does not exceed a predefined maximum level, this last set of relative component proportions then being retained as yielding the mixture of the selected pH at the given salt concentration. In alternative embodiment, the convergence criteria may e.g. be selected as a fixed number of iterations, or other suitable relations. In a specific embodiment, the procedure above is iterated less than 10 times, preferably less than 8 times and more preferably 4-6 times, such as 5 times.

In certain embodiments, the chromatogram is obtained through elution with a gradient in pH and/or conductivity. The gradient can be a linear gradient, but it can also be a non-linear gradient. It can further be a step gradient, where the pH and/or conductivity is rapidly changed from a start condition to an end condition.

In some embodiments the concentrations of the acid and base forms are calculated from pH values determined from the composition of the buffer. This can be done using the Debye-Hückel equation in combination with the Henderson-Hasselbach equation as discussed above.

In certain embodiments, the chromatography system further comprises a pH detector downstream of said chromatography column and the concentrations of the acid and base forms are calculated from pH values measured by the pH detector. At low ionic strengths, the activity coefficients $\varphi$ can be approximated with 1 and the concentrations can be calculated directly from the Henderson-Hasselbach equation. If the chromatography system further comprises a conductivity detector downstream of the chromatography column, conductivity values measured by this detector can be used to estimate the ionic strength and thus allow a more exact calculation of the activity coefficients $\varphi$ using the using the Debye-Hückel equation as discussed above. This allows high precision calculation of the concentrations of the acid and base forms also at higher ionic strengths, which may be encountered particularly in ion exchange and hydrophobic interaction chromatography techniques. The estimation of the ionic strength from conductivity values can use empirical correlations, e.g. the Russell correlation as described in Russell, L. L., 1976, Chemical Aspects of Groundwater Recharge with Wastewaters, Ph.D. Thesis, University of California at Berkeley. Alternatively, the ionic strength may be calculated from values of conductivity and pH with knowledge about the composition of the buffer, using the methods disclosed in US20130270492, hereby incorporated by reference in tis entirety. Briefly, this involves calculating the Kohlrausch coefficients and the molar conductivities for all the species present in the buffer, including $H^+$ and $OH^-$ which have particularly high molar conductivities.

In some embodiments, the wavelength $\lambda$ is within the range of 190-290 nm, such as 190-260 nm, 200-240 nm or 210-230 nm 280 nm is a commonly used wavelength for detectors in liquid chromatography. Although buffering species with significant absorption at 280 nm have often been avoided due to issues with pH-induced baseline shifts, the corrections of the invention provide a possibility to use such species. At lower wavelengths, many commonly used buffering species, e.g. carboxylic acids and their salts, have significant pH-dependent absorption, with a corresponding need for baseline correction. This applies e.g. to common buffering species like citrates and acetate.

In certain embodiments, UV extinction coefficients and the dissociation constant(s) are retrieved from a computer readable medium. Suitably, the correction method can be performed by a control unit such as a computer.

In a second aspect, the current invention discloses a computer program on a tangible readable medium for correcting a baseline in a chromatogram according to the method as described in any of the above embodiments.

Figure 4:
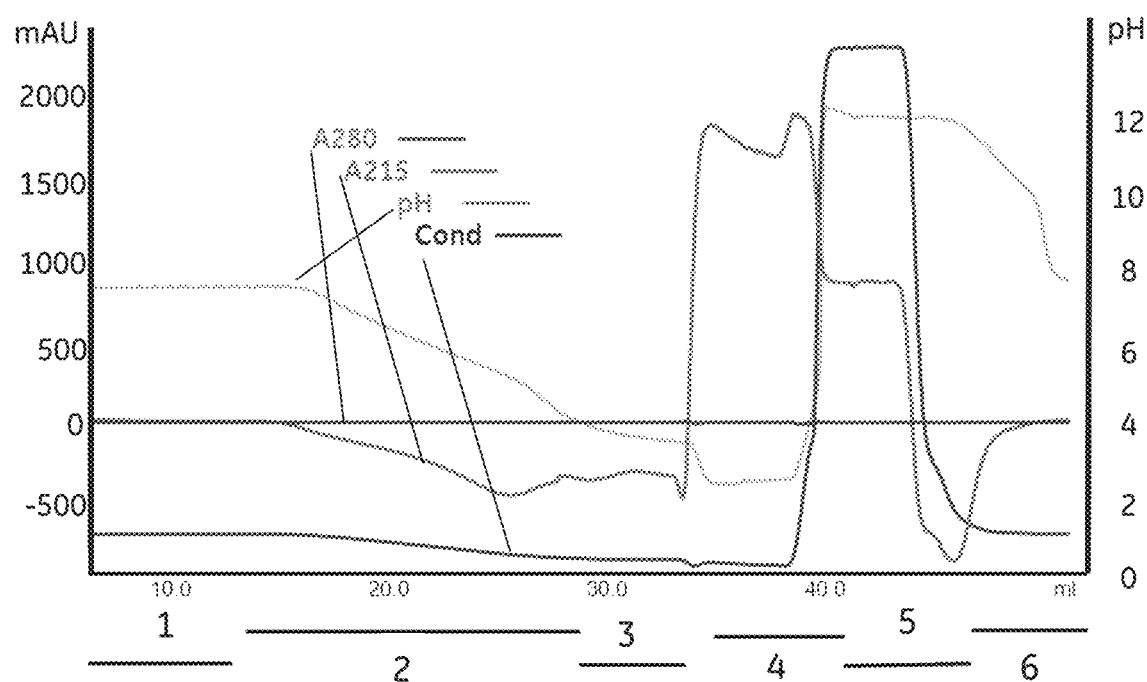
FIG. 4 shows a chromatogram with UV responses at 215 and 280 nm wavelength and measured pH and conductivity values. 1-20 mM citric acid, 20 mM $NaH_2PO_4$, pH 7.6. A280 and A215 at zero (baseline), 2-20 mM citric acid, 20 mM $NaH_2PO_4$, pH gradient 7.6-3.5. A280 zero, A215 zero to −450 mAU, parallel with pH gradient, 3-20 mM citric acid, 20 mM $NaH_2PO_4$, pH 3.5. A280-400 mAU. 4-0.5 M acetic acid. A280 zero, A215 to 1900 mAU, 5-0.5 M NaOH. A280 zero, A215 to 1900 mAU, 6-20 mM citric acid, 20 mM $NaH_2PO_4$, pH 7.6. A280 and A215 return to zero.
Figure 5:
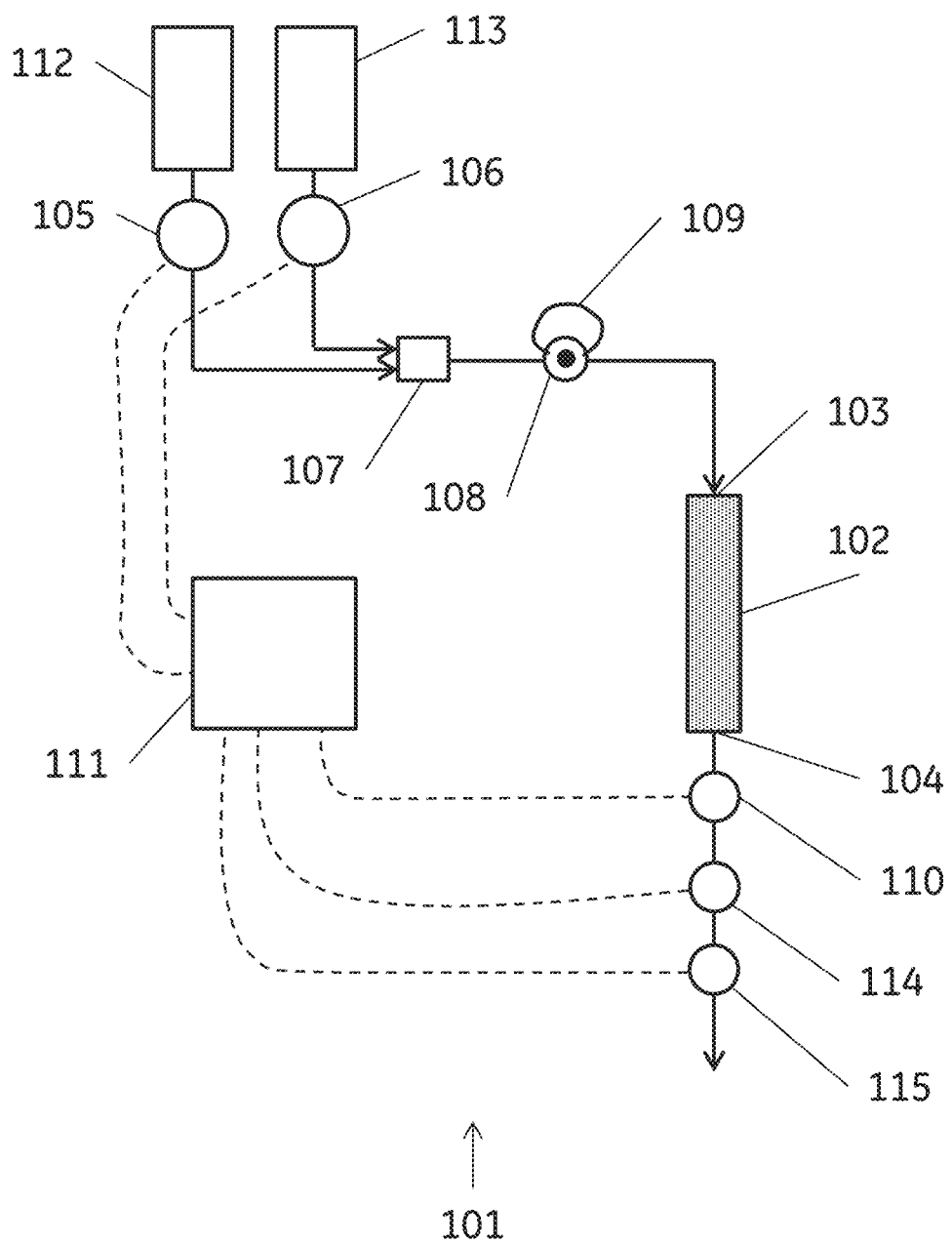
FIG. 5 shows a chromatography system for use with the method of the invention.

In a third aspect, the current invention discloses a chromatography system 101 arranged to perform the method of any one of the embodiments as described above. The system can e.g. be arranged as illustrated in FIG. 4, which shows a chromatography column 102 with an inlet 103 and an outlet 104, at least one pump, such as a first 105 and a second 106 pump, a mixer 107, a sample injection valve 108 with an injection loop 109, a UV detector 110 and a control unit 111. The system may further comprise a first 112 and a second 113 buffer reservoir, a pH detector 114 and a conductivity detector 115. During normal operation the first and second pumps are controlled by the control unit and deliver a first and a second buffer from the first and second buffer reservoirs at determined flow rates to the mixer. There they are mixed to form a mobile phase buffer which is conveyed to the column and through the UV detector, the pH detector and the conductivity detector, where output signals from the three detectors are transmitted to the control unit. When a sample is injected with the injection valve it is conveyed through the column and, depending on how the components of the sample interact with the column, the components will exit the column at different points of time and will be detected by the UV detector. During elution of the column, the composition of the mobile phase buffer can be varied by changing the relative flow rates between the first and second pumps according to signals from the control unit. The actual composition of the mobile phase buffer after passage of the column can be monitored by the pH detector and the conductivity detector. Typically, the system is initially equilibrated by pumping a loading buffer (also called A buffer) from one of the buffer reservoirs as the mobile phase buffer through the system and the sample is injected. Some time after injection of the sample, the mobile phase buffer composition can be changed by either switching to an elution buffer (also called B buffer) from the other buffer reservoir, producing a step gradient, or by applying an increasing gradient of B buffer (with a corresponding decreasing gradient of A buffer). The elution or B buffer typically has a different ionic strength and/or a different pH value than the loading or A buffer.

The control of the mobile phase buffer composition can be provided by the control unit. In some embodiments this is done by controlling the first and second pumps, e.g. by a) switching off the first pump and switching on the second pump to obtain a step gradient, b) linearly decreasing the flow rate of the first pump and linearly increasing the flow rate of the second pump to obtain a linear buffer gradient or c) changing the relative flow rates of the pumps according to predetermined non-linear functions to obtain a non-linear gradient. For improved control of the pH and conductivity of the mobile phase buffer delivered to the column, the methods described in US20110039712 and/or US20130270492 can be used to calculate the mixing ratio of the buffers (and the corresponding pump flow rate ratios) needed to obtain specific values of pH and/or conductivity in the mobile phase buffer. These calculations can be made continuously to provide a predetermined pH and/or conductivity gradient, with the pump flow rates changed to provide the predetermined pH/conductivity at any given point in time. As described above, the calculation of the required mixing ratios can also involve a calculation of the concentrations of any UV-absorbing weak acids and bases at the predetermined pH/conductivity conditions, which may in turn be used to calculate the UV absorbance of the weak acids and bases at the wavelength $\lambda$ of the UV detector and. The calculated absorbances can then be subtracted from the measured UV absorbances to provide a corrected baseline.

Alternatively, the signals pH detector and the conductivity detector can be used by the control unit to calculate the UV absorbance of the weak acids and bases at the wavelength $\lambda$ of the UV detector. The conductivity signal in combination with the pH signal can be used to calculate or estimate the ionic strength and thus the activity coefficients of the UV-absorbing weak acids and bases, such that the concentrations of the weak acids and bases can be calculated from the dissociation constants. Using known extinction coefficients at wavelength $\lambda$, the total UV absorbance of the weak acids and bases in the mobile phase buffer can be calculated and subtracted from the measured absorbance at wavelength $\lambda$ from the UV detector to obtain a corrected baseline. An advantage of using the post-column measured pH and conductivity as a basis for the baseline correction is that also pH variations induced by flowing salt solutions through ion exchange columns can be accounted for. Such pH variations are described e.g. in S Ghose et al: Biotechnol Progr 18, 530-537, 2002.

All these operations can be controlled by the control unit, which may comprise a computer program on a tangible readable medium with instructions to carry out the methods described above.

Example 1 (FIG. 3)

A column packed with the anion exchanger Capto™ Q (GE Healthcare) was equilibrated with a 20 mM citric acid and 20 mM NaH$_2$PO$_4$ buffer adjusted to pH 7.6 with NaOH (stage 1) and the 215 and 280 nm detectors were adjusted to zero. A pH gradient of pH 7.6-pH 3.5 in 20 mM citric acid and 20 mM NaH$_2$PO$_4$ buffer was then applied (stage 2), which resulted in a stable baseline at 280 nm but a significant downward shift in the 215 nm absorbance due to the lower 215 nm extinction coefficient of citric acid/acidic citrate ions in comparison with basic citrate ions. After the gradient, an isocratic solution of 20 mM citric acid and 20 mM NaH$_2$PO$_4$ buffer pH 3.5 was applied (stage 3), with the 215 nm absorbance at approx. −400 mAU. When 0.5 M acetic acid was applied to the column (stage 4) the absorbance at 280 nm was still zero, while the 215 nm absorbance increased sharply due to the 215 nm absorption of acetic acid. The mobile phase was then shifted to 0.5 M NaOH (stage 5) and the 215 nm absorbance decreased to a plateau level corresponding to the 215 nm absorption of NaOH. Finally, the column was reequilibrated with 20 mM citric acid and 20 mM NaH$_2$PO$_4$ buffer adjusted to pH 7.6 (stage 6) and the 215 nm absorbance returned to zero after a negative excursion.

Example 2

For a number of buffer systems with pH-dependent UV absorption the UV spectra were taken up in a 1 cm flow cell.

The lower UV cutoff wavelength (defined as the wavelength where transmission is reduced by 50% compared to high wavelengths) was listed in Table 1 for some selected systems.

| Buffer system | UV cutoff |
|---|---|
| AIEX - mix BisTris HCl-Tris pH 5.3 with 1M NaCl | 232 nm |
| AIEX - mix BisTris HCl-Tris pH 7.4 with 0.5M NaCl | 255 nm |
| AIEX - mix BisTris HCl-Tris pH 9.5 with 0M NaCl | 255 nm |
| HCl - Diethanolamine pH 8.4 with 1M NaCl | 207 nm |
| HCl - Diethanolamine pH 8.8 with 0.4M NaCl | 211 nm |
| HCl - Diethanolamine pH 10 | 218 nm |
| HCl - Ethanolamine pH 8.8 | 203 nm |
| HCl - Ethanolamine pH 9.3 with 0.5M NaCl | 208 nm |
| HCl - Ethanolamine pH 10.5 with 1M NaCl | 213 nm |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if they were individually incorporated.

The invention claimed is:

1. A method for correcting a baseline in a chromatogram using a buffer with at least one UV-absorbing component which is a weak acid or a weak base, the method comprising the steps of:
   a) providing a chromatography system comprising:
      (i) a chromatography column;
      (ii) a pH detector located downstream of an outlet of the chromatography column and configured for measuring the pH values;
      (iii) a UV detector located between the chromatography column outlet and the pH detector;
      (iv) a conductivity connector located downstream of the pH detector and configured for measuring an ionic strength the buffer; and
      (v) a control unit having one end connected to a first pump and a second pump of the chromatography column and a second end connected to the UV detector, the pH detector, and the conductivity detector, the control unit being configured to control the pumps and to receive and measure signals from the detectors;
   b) during operation, controlling, at the control unit, a mobile phase buffer composition, by:
   (i) switching off the first pump and switching on the second pump to obtain a step gradient; (ii) linearly decreasing the flow rate of the first pump and linearly increasing the flow rate of the second pump to obtain a linear buffer gradient; or (iii) changing the relative flow rates of the first pump and the second pump according to predetermined non-linear function to obtain a non-linear gradient;
   (c) mixing a first buffer and a second buffer delivered at determined flow rates by the first and second pumps, respectively, to form the mobile phase buffer composition to be conveyed to the chromatography column through the UV detector, the pH detector and the conductivity detector, by calculating a mixing ratio of the first buffer and the second buffer needed to obtain predetermined values of pH and conductivity;
   (d) injecting a sample having components, via an injection valve, through the chromatography column, each component exiting the chromatography column at a different point of time and being detected by the UV detector;
   (e) providing, at the control unit, UV extinction coefficients for a weak acid form and a weak base form of the at least one UV-absorbing component and a dissociation constant for the UV-absorbing component;
   (f) obtaining a chromatogram having UV absorption data from the UV detector under a set of conditions where a range of pH and/or a conductivity values are measured;
   (g) calculating, at the control unit, concentrations of the weak acid and weak base forms of the at least one UV absorbing buffer component under the set of conditions used in the chromatogram; and
   (h) calculating, via the pH and conductivity signals measured by the control unit, UV absorption values of the acid and base forms under the same set of conditions and subtracting the calculated UV absorption values from the UV absorption values measured by the control unit.

2. The method of claim 1, wherein the concentrations of the acid and base forms are calculated using the equation of Debye-Huckel.

3. The method of claim 2, wherein an ion size parameter a in the Debye-Huckel equation is determined as a weighted mean ion size of all species contributing significantly to the ionic strength of the buffer, and wherein the ionic strength of each of the species is used as weighting parameter.

4. The method of claim 3, wherein the ion size parameter a of the Debye-Huckel equation is determined as $$a = \frac{\sum I_i a_i}{I},$$

wherein $I_i$, is the ionic strength and $a_i$ is the ion size parameter of species i and I the total ionic strength.

5. The method of claim 2, wherein the ion size parameter a of the Debye-Huckel equation is approximated as $a=0.5*(mass)^{1/3}+shell$,
   wherein "shell" is fixed at one value for a positively charged species and fixed at a different value for a negatively charged species, and fixed at a value in the range of 3.8-4.2 for positively charged ionic species; and "shell" is fixed at a value in the range of 0-0.2 for negatively charged ionic species.

6. The method of claim 1, wherein the concentrations of said acid and base forms are calculated using an iterative procedure.

7. The method of claim 6, wherein the iterative procedure comprises:
   i) determining the concentrations wherein a pre-defined ionic strength of the liquid mixture is addressed to the species according to a pre-defined distribution among the species;

ii) on the basis of the concentrations determined in the preceding step, calculating the ionic strength of each species in the buffer;

iii) determining a new set of concentrations; taking account of the ionic strength calculated in ii), and iv) repeating the steps ii) and iii) until a predetermined convergence criterion is met.

8. The method of claim 1, wherein the chromatogram is obtained through elution with a gradient in pH and/or conductivity.

9. The method of claim 1, wherein the concentrations of the acid and base forms are calculated from pH values determined from the composition of the buffer.

10. The method of claim 1, wherein the concentrations of the acid and base forms are calculated from pH values measured by the pH detector.

11. The method of claim 1, wherein the wavelength X is within the range of 190-260 nm.

12. The method of claim 1, wherein the UV extinction coefficients and the dissociation constant are retrieved from a readable medium.

13. A computer program on a non-transitory computer readable medium for correcting a baseline in a chromatogram according to the method of claim 1.

14. A chromatography system arranged to perform the method of claim 1.

* * * * *